United States Patent
Murakami et al.

(10) Patent No.: US 11,642,152 B2
(45) Date of Patent: May 9, 2023

(54) CANNULA HOLDER

(71) Applicant: MANI, Inc., Utsunomiya (JP)

(72) Inventors: Etsuo Murakami, Utsunomiya (JP); Masanori Oshino, Utsunomiya (JP)

(73) Assignee: MANI, Inc., Utsunomiya (JP)

( * ) Notice: Subject to any disclaimer, the term of this patent is extended or adjusted under 35 U.S.C. 154(b) by 135 days.

(21) Appl. No.: 16/634,575

(22) PCT Filed: Jul. 27, 2018

(86) PCT No.: PCT/JP2018/028232
§ 371 (c)(1),
(2) Date: Jan. 28, 2020

(87) PCT Pub. No.: WO2019/026787
PCT Pub. Date: Feb. 7, 2019

(65) Prior Publication Data
US 2021/0093351 A1  Apr. 1, 2021

(30) Foreign Application Priority Data

Jul. 31, 2017 (JP) .............................. JP2017-147886

(51) Int. Cl.
*A61B 17/34* (2006.01)
*A61F 9/007* (2006.01)

(52) U.S. Cl.
CPC ...... *A61B 17/3421* (2013.01); *A61B 17/3462* (2013.01); *A61F 9/007* (2013.01)

(58) Field of Classification Search
CPC ............ A61B 17/3421; A61B 17/3462; A61B 17/3423; A61B 17/3431; A61B 17/3417;
(Continued)

(56) References Cited

U.S. PATENT DOCUMENTS 3,659,607 A * 5/1972 Banko ................. A61F 9/00745
606/169
6,099,505 A   8/2000 Ryan et al.
(Continued)

FOREIGN PATENT DOCUMENTS

| JP | 2009502211 A | 1/2009 |
| JP | 2016179182 A | 10/2016 |
| WO | 2010126076 A1 | 11/2010 |

OTHER PUBLICATIONS

International Search Report (ISR) for Application No. PCT/JP2018/028232 dated Oct. 23, 2018.
(Continued)

*Primary Examiner* — Erich G Herbermann
(74) *Attorney, Agent, or Firm* — Isshiki & Partners; Joseph P. Farrar, Esq.

(57) ABSTRACT

A cannula holder capable of securing a cannula to the holder at the time of piercing work, and easily removing the cannula from the holder using tweezers or the like. The cannula holder, to which a piercing needle for piercing an eyeball and a cannula are attached when attaching the cannula used in ophthalmic operations to the eyeball, includes claw portions that are formed on a front end of the cannula holder and which press sides of the cannula either at positions where said claw portions face each other or from multiple directions. A depression may be provided in a side of the front end of the cannula holder, allowing visibility of a part of a back end of the cannula from the depression.

1 Claim, 5 Drawing Sheets

(58) Field of Classification Search
CPC . A61B 17/34; A61B 17/3496; A61B 17/3468;
A61B 2017/3425; A61B 2017/3427;
A61B 2017/3429; A61B 2017/3433;
A61B 2017/3435; A61B 2017/3437;
A61B 2017/3441; A61B 2017/3443;
A61B 2017/3445; A61B 2017/3447;
A61B 2017/3449; A61B 2017/345; A61B
2017/3452; A61F 9/007; A61F 9/00736;
A61F 9/013; A61M 2005/1585
See application file for complete search history.

(56) References Cited

U.S. PATENT DOCUMENTS

| | | | | |
|---|---|---|---|---|
| 6,764,439 | B2* | 7/2004 | Schaaf | A61F 9/00781 600/106 |
| 2006/0089526 | A1* | 4/2006 | Chen | A61B 1/00142 600/101 |
| 2006/0264992 | A1 | 11/2006 | Franer et al. | |
| 2008/0033462 | A1* | 2/2008 | Di Nardo | A61F 9/007 606/166 |
| 2009/0240204 | A1* | 9/2009 | Taylor | A61B 17/3462 604/167.03 |
| 2010/0160938 | A9 | 6/2010 | Franer et al. | |
| 2011/0152774 | A1 | 6/2011 | Lopez et al. | |
| 2012/0165851 | A1* | 6/2012 | Murakami | A61B 17/3421 606/185 |
| 2012/0302961 | A1 | 11/2012 | Lopez et al. | |
| 2015/0038893 | A1* | 2/2015 | Haffner | A61F 9/0017 604/8 |

OTHER PUBLICATIONS

Translation of the ISR for Application No. PCT/JP2018/028232 dated Oct. 23, 2018.
Written Opinion of the International Search Authority for Application No. PCT/JP2018/028232 dated Oct. 23, 2018.

* cited by examiner

CANNULA HOLDER

CROSS REFERENCE TO RELATED APPLICATIONS

The present application is a national phase entry under 35 U.S.C. § 371 of International Application No. PCT/JP2018/028232, filed on Jul. 27, 2018, which claims priority from Japanese Application No. 2017-147886, filed on Jul. 31, 2017, the entire disclosures of which are hereby incorporated by reference herein.

TECHNICAL FIELD

The present invention relates to a cannula holder (hereafter referred to as 'holder') used when attaching a cannula used in ophthalmic operations to an eyeball.

BACKGROUND ART

The cannula is attached to an eyeball, and a surgical tool or the like is passed through the cannula when using a surgical tool or the like within an eyeball during an ophthalmic operation (e.g., Patent Document 1). FIG. 5 is a cross-section of a conventional cannula, and FIG. 6 is diagram illustrating how an ophthalmic operation is performed. A cannula 20 is configured by fitting a metal pipe 21 into a base 22 made of resin, and covering and enveloping a cylindrical side surface of the base 22 and the base end of the pipe 21 by a cap 23 made of silicone rubber.

The base 22 has a function of a stopper by touching the surface of an eyeball E when the pipe 21 is pierced in the eyeball E, and the cap 23 has a function of controlling leakage of vitreous humor, etc., from the inside of the eyeball E. The base 22 has a nearly cylindrical shape and a groove 22a formed along the circumference near the middle position of its side surface. The groove 22a is used to hold the cannula 20 with tweezers, and to fit in a locking part 23b of the cap 23 when covering the base 22 with the cap 23.

The cap 23 has a slit 23a, which connects the inner side of the pipe 21 and the outer side of the cap 23, provided in a portion that covers a base end of the pipe 21, and may be provided with a piercing needle used for piercing the eyeball E by passing through the slit 23a, or otherwise various surgical tools 40, optical instruments for monitoring, etc., may be inserted in the eyeball E through the slit 23a.

FIG. 7 is a diagram describing a method of attaching the cannula to an eyeball, wherein FIG. 7(a) illustrates a state before piercing, FIG. 7(b) illustrates a state after piercing, and FIG. 7(c) illustrates a state of cannula attachment completion.

Since the cannula 20 is a very small tool, it is attached to a front end of the holder 100 so as to carry out attachment when being attached to the eyeball E. At this time, a piercing needle 30 for piercing the eyeball E is also attached to the holder 100 with the piercing needle passing through the pipe 21 of the cannula 20 (state of FIG. 7(a)). The piercing needle 30 and the pipe 21 of the cannula 20 as one body pierce the eyeball E (state of FIG. 7(b)). The holder 100 and the piercing needle 30 are then removed from the cannula 20, leaving only the cannula 20 piercing the eyeball E (state of FIG. 7(c)).

PRIOR ART DOCUMENTS

Patent Documents

[Patent Document 1] WO 2010/126076A

DISCLOSURE OF THE INVENTION

Problem to be Solved by the Invention

Here, the cannula needs to be secured to the front end of the holder during the attachment since the cannula is attached to the eyeball with both of the cannula and the piercing needle attached to the holder. However, since the cannula needs to be removed from the holder while the cannula is piercing the eyeball, there is fear that if it is secured too firmly, a problem that the cannula will detach from the eyeball when removing the holder will occur.

In light of this problem, the present invention aims to provide a cannula holder allowing stable attachment of securely attaching a cannula to a holder front end, and also allowing easy removal of the cannula from the holder after the cannula is attached to an eyeball.

Solution to the Problem

A cannula holder is characterized by having a cannula and a piercing needle for piercing an eyeball attached thereto when attaching the cannula used in ophthalmic operations to the eyeball. It includes claw portions that are formed on a front end of the cannula holder and press sides of the cannula either at positions where said claw portions face each other or from multiple directions.

It may have a configuration including a depression in a side of the front end of the cannula holder, allowing visibility of a part of a back end of the cannula from the depression.

Moreover, the cannula should include a resin cap including a slit through which the piercing needle passes at a back end of the cannula, and when the piercing needle has a thin, approximately oblong cross-section that fits together with the form of the slit at a position that allows the piercing needle to pass through the slit, the claw portions are provided at positions to apply pressing forces perpendicularly toward the long sides facing each other of the approximately oblong cross-section of the piercing needle, or similarly, the claw portions are provided at positions to apply pressing forces from multiple directions toward the sides of the circular cross-section with the reduced diameter of the piercing needle.

Advantageous Effect of the Invention

According to the present invention, the beneficial results are that the cannula may be secured to the holder at the time of piercing, and yet the cannula may also be easily removed from the holder using tweezers or the like.

Moreover, the claw portions pressing in directions that allow easy bending of the piercing needle allow stable attachment.

BRIEF DESCRIPTION OF DRAWINGS

FIG. 1 is an oblique view of a holder of the present invention, wherein FIG. 1(a) illustrates only the holder, FIG. 1(b) illustrates a state where a piercing needle is attached to the holder, and FIG. 1(c) illustrates a state where a piercing needle and a cannula are attached to the holder;

FIG. 2 is an oblique view of a different holder of the present invention, wherein FIG. 2(a) illustrates only the holder, and FIG. 2(b) illustrates a state where a piercing needle is attached to the holder;

FIG. 7 is a diagram describing a method of attaching the cannula to an eyeball, wherein FIG. 7(a) illustrates a state before piercing, FIG. 7(b) illustrates a state after piercing, and FIG. 7(c) illustrates a state of cannula attachment completion.

DESCRIPTION OF EMBODIMENTS

An embodiment according to the present invention is described below with reference to accompanying drawings.

Figure 1:
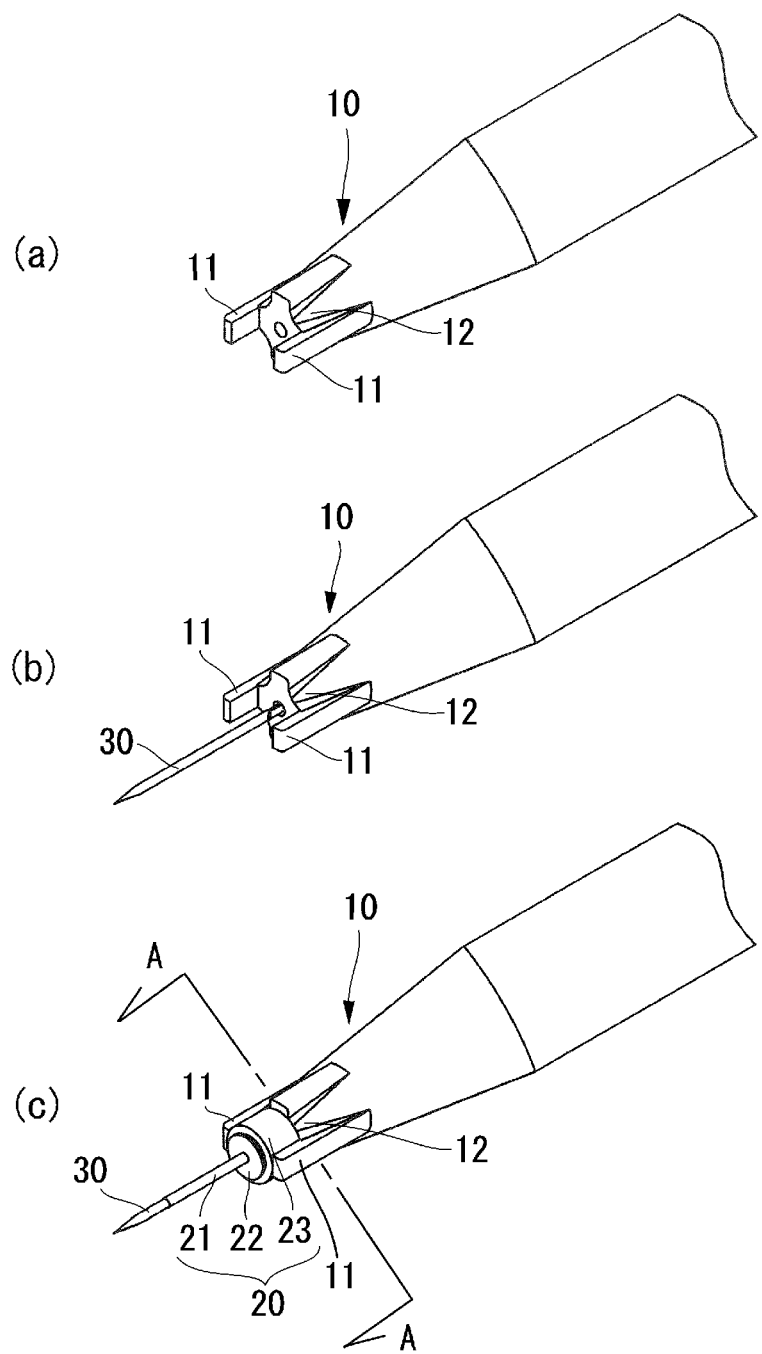

FIG. 1 is an oblique view of a holder of the present invention, wherein FIG. 1(a) illustrates only the holder, FIG. 1(b) illustrates a state where a piercing needle is attached to the holder, and FIG. 1(c) illustrates a state where a piercing needle and a cannula are attached to the holder.

A cannula holder 10 of the present invention, to which a piercing needle 30 and a cannula 20 for piercing an eyeball during an ophthalmic operation are attached, is used when attaching the cannula 20 to the eyeball.

The cannula 20 is configured in the same manner as the conventional cannula by fitting a metal pipe 21 into a base 22 made of resin, and covering and enveloping a cylindrical side surface of the base 22 and the base end of the pipe 21 by a cap 23 made of silicone rubber. Since such a cannula 20 is small, it is difficult to pinch with fingers, and is thus attached to the holder 10 so as to facilitate attachment to the eyeball.

Moreover, the piercing needle 30 is used for piercing the eyeball. The base end side of the piercing needle 30 is secured to the holder 10 with the point of the needle protruding from the pipe 21 of the cannula 20. It then pierces the eyeball with the piercing needle 30 and the pipe 21 united as one body. Therefore, during the piercing work, the piercing needle 30 and the cannula 20 need to be tightly secured to the holder 10.

As a result, claw portions 11 for securing the cannula 20 are provided on a front end of the holder 10. The claw portions 11 of FIG. 1 are configured so as to press the sides of the cannula 20 at positions where the claw portions face each other. In other words, the claw portions 11 are made to clamp sides of the cap 23 of the cannula 20.

There may be two pairs or more of the claw portions 11, and increasing the number of pairs thereof allows further tightly securing of the cannula 20 to the holder 10. However, if the cannula 20 is secured too tightly, there is concern that the cannula 20 will detach from the eyeball when removing the cannula 20 from the holder 10. Therefore, since removal of the cannula 20 becomes difficult when there are too many pairs of the claw portions 11, one pair is preferable, and up to two pairs may be used. There is an advantage particularly with one pair of the claw portions 11 in that the cap 23 of the cannula 20 is easily clamped using tweezers or the like when removing the cannula 20 from the holder 10.

Figure 2:
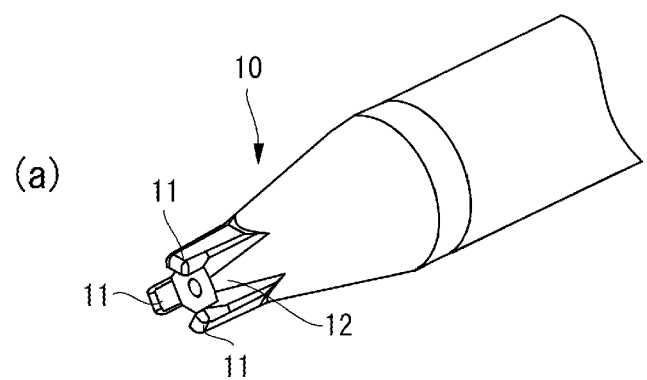
Figure 2:
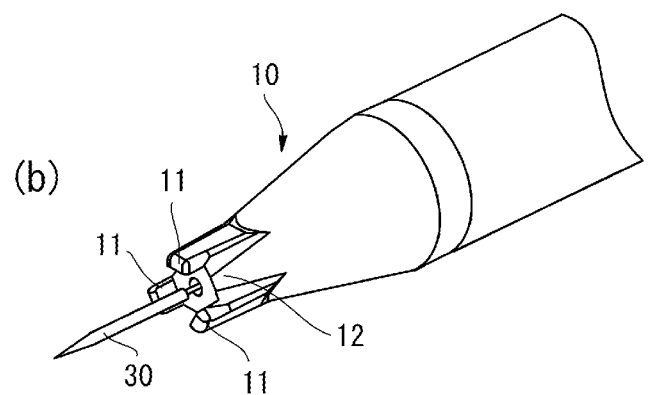

FIG. 2 is an oblique view of a different holder of the present invention, wherein FIG. 2(a) illustrates only the holder, and FIG. 2(b) illustrates a state where a piercing needle is attached to the holder. There are three of the claw portions 11 in this working example. With such a configuration, the claw portions 11 are not at positions facing each other, but they may press and secure the cannula 20 from the sides in a well-balanced manner. Note that the number of the claw portions 11 is not limited to three. That is, as long as the cannula 20 can be secured to the holder, the number of the claw portions 11 pressing from multiple directions is not necessarily limited. However, as described above, since removal of the cannula 20 becomes difficult when there are too many of the claw portions 11, around three are appropriate.

A depression 12 is formed in a side of the front end of the holder 10 illustrated in FIG. 1 and FIG. 2. The depression 12 is provided for facilitating removal of the cannula 20 from the holder 10 using tweezers or the like.

Figure 3:
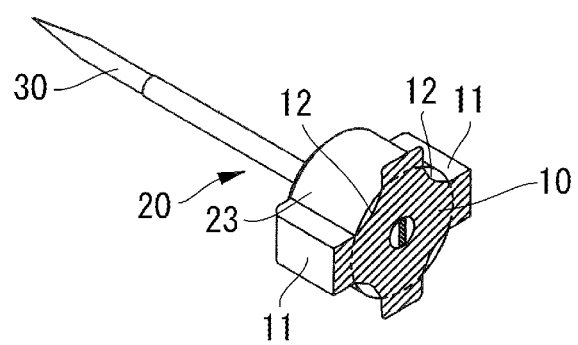
FIG. 3 is a cross-section cut along a line A-A of FIG. 1(c)

FIG. 3 is a cross-section cut along a line A-A of FIG. 1(c). As can be confirmed from the drawings, it is configured such that a part of a back end surface of the cannula 20 is visible from the position of the depression 12. That is, since tweezers or the like may be positioned on the depression 12, pressing the cap 23 of the cannula 20 from the back end is possible, thereby making it easy to remove the cannula 20 from the holder 10. Note that while the number of the depression 12 is not limited, if the depression 12 is, for example, in two places, it becomes possible to push the back end of the cannula 20 from two places using two front ends of the tweezers. Therefore, multiple depressions are preferable.

Figure 4:
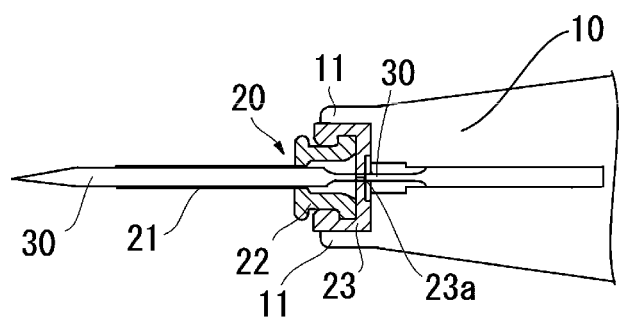
FIG. 4 is a cross-section of the piercing needle and the cannula attached to the holder.
Figure 5:
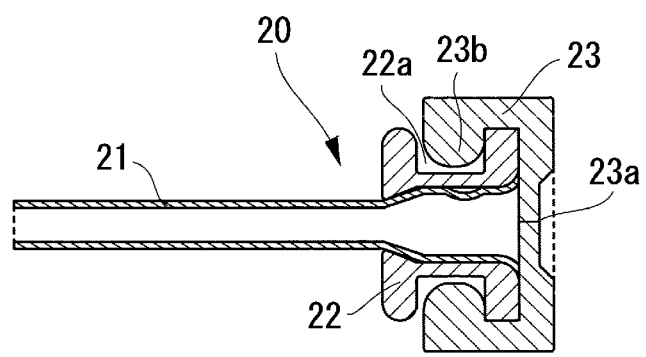
FIG. 5 is a cross-section of a conventional cannula.
Figure 6:
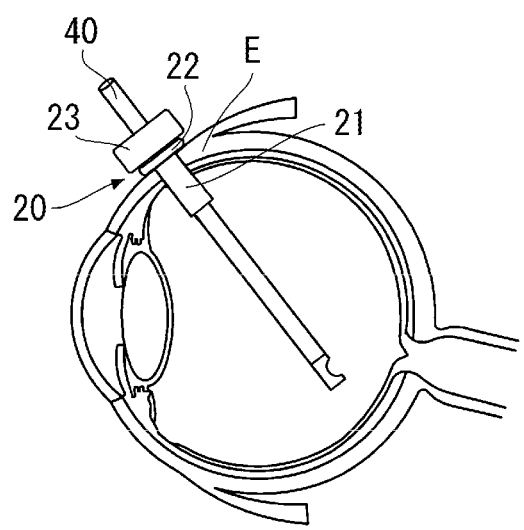
FIG. 6 is diagram illustrating how an ophthalmic operation is performed.
Figure 7:
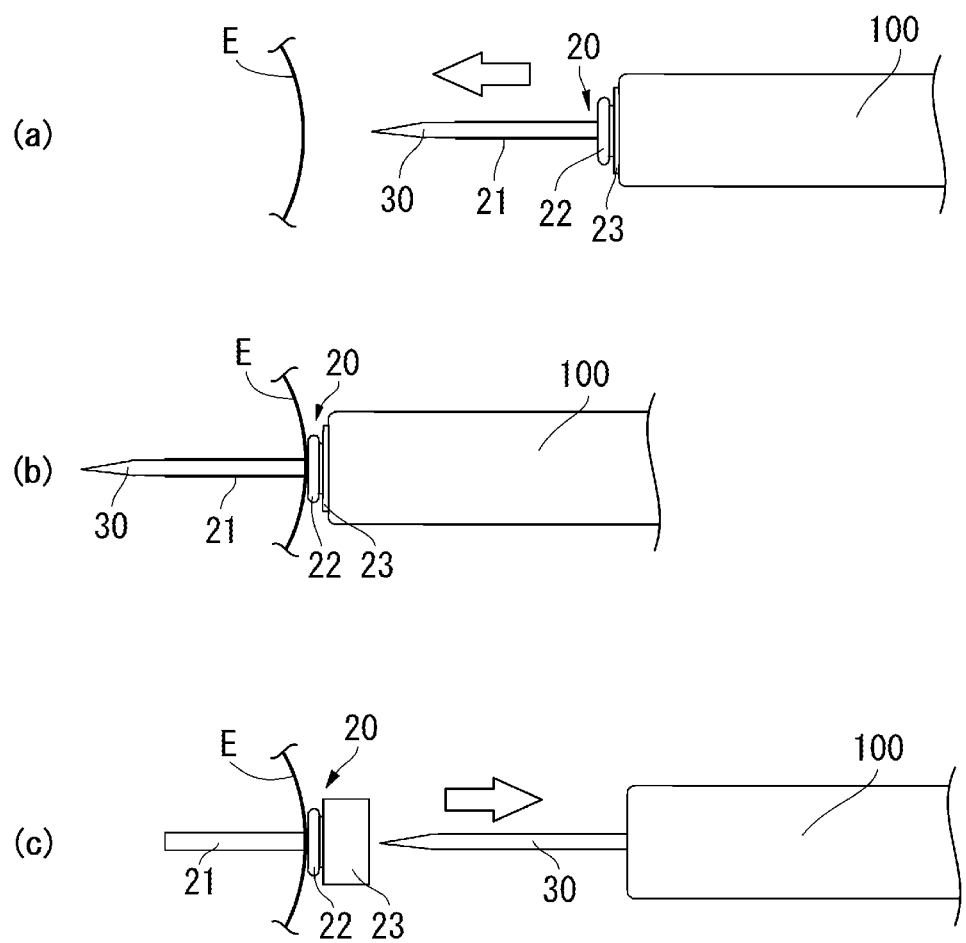

FIG. 4 is a cross-section of the piercing needle and the cannula attached to the holder. The cannula 20 here has a resin cap 23 including a slit 23a through which the piercing needle 30 passes at the back end of the cannula 20. Moreover, the piercing needle 30 has a thin, approximately oblong cross-section fitted together with the form of the slit 23a at a position for passing therethrough. Such a structure allows control of deformation of the slit 23a to a minimum, and even after the piercing needle 30 is pulled out, the slit 23a is hardly spread open at all, making it possible to control leakage of vitreous humor, etc., from the eyeball.

In the case of the piercing needle 30 made to have a small cross-section at the position of the slit 23a in this manner, it is weak when bent with a thin approximately oblong cross-section, and thus there is concern that the point of the piercing needle 30 moves when piercing, making it difficult to pierce at a precise position. However, provision of the claw portions 11 at positions to apply pressing forces perpendicularly toward the long sides facing each other of the approximately oblong cross-section of the piercing needle 30 can suppresses bending of the piercing needle 30.

The cross-sectional form of the piercing needle 30 at the position that allows the piercing needle to pass through the slit 23a may have a different shape than a thin, approximately oblong shape. For example, it may be a circular cross-section with a reduced diameter (see FIG. 2(b)). In such a case, since the piercing needle 30 is weakened with bending in any direction, the claw portions 11 should be provided at positions to apply pressing forces from multiple directions toward the sides of the circular cross-section with the reduced diameter.

Use of such a cannula holder allows sufficient securing of a cannula to the holder at the time of piercing work, and allows easy removal of the cannula from the holder using tweezers or the like. Moreover, the claw portions pressing in directions that otherwise allow easy bending of the piercing needle enable secure attachment.

EXPLANATION OF REFERENCE NUMERALS

10: Cannula holder
11: Claw portion
12: Depression
20: Cannula

21: Pipe
22: Base
22a: Groove
23: Cap
23a: Slit
30: Piercing needle
40: Surgical tool
E: Eyeball

The invention claimed is:

1. A cannula holder used in ophthalmic operations, the cannula holder comprising:
   a cannula;
   a piercing needle configured to pierce an eyeball upon attachment of the cannula to the eyeball, whereupon the piercing needle is removed from the cannula together with the holder;
   the cannula including a resin cap with a slit through which the piercing needle passes at a back end of the cannula; and
   claw portions that are formed on a front end of the cannula holder and which clamp sides of the cannula at positions where said claw portions face each other,
   wherein the piercing needle is manufactured to have an approximately oblong cross-section that fits together with a form of the slit at a position that allows the piercing needle to pass through the slit, and
   the claw portions are provided at positions to apply clamping forces perpendicularly toward opposed long sides of the approximately oblong cross-section of the piercing needle via pressing on the cannula so as to suppress bending of the piercing needle, the claw portions extending toward a front end of the needle beyond where the needle pierces the slit,
   the cannula holder further comprising a sloped front end face of gradually narrowing circumference toward a tip thereof for accommodating the cannula therein, the tip having a circumference smaller than a circumference of the back end of the cannula holder,
   the cannula holder further including multiple elongated depressions, tapered so as to narrow toward the front end of the cannula holder, disposed between the claw portions at regular radial intervals around lateral sides of the front end of the cannula holder.

* * * * *